(12) United States Patent
Matwiejuk et al.

(10) Patent No.: US 10,899,782 B2
(45) Date of Patent: *Jan. 26, 2021

(54) SEPARATION OF OLIGOSACCHARIDES FROM FERMENTATION BROTH

(71) Applicant: GLYCOM A/S, Hørsholm (DK)

(72) Inventors: Martin Matwiejuk, Hamburg (DE); Nikolay Khanzhin, Humlebæk (DK); Pierre Chassagne, Beaumont (FR); Markus Jondelius Hederos, Trelleborg (SE)

(73) Assignee: GLYCOM A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/082,848

(22) PCT Filed: Mar. 7, 2017

(86) PCT No.: PCT/DK2017/050063
§ 371 (c)(1),
(2) Date: Sep. 6, 2018

(87) PCT Pub. No.: WO2017/152918
PCT Pub. Date: Sep. 14, 2017

(65) Prior Publication Data
US 2019/0031698 A1     Jan. 31, 2019

(30) Foreign Application Priority Data
Mar. 7, 2016    (DK) .................. 2016 70131

(51) Int. Cl.
| | | |
|---|---|---|
| C07H 1/08 | (2006.01) |
| C07H 1/06 | (2006.01) |
| B01D 61/14 | (2006.01) |
| C08B 37/00 | (2006.01) |
| B01D 61/16 | (2006.01) |
| C07H 13/04 | (2006.01) |
| A23L 33/195 | (2016.01) |
| B01D 15/36 | (2006.01) |
| C07H 23/00 | (2006.01) |
| C12P 19/04 | (2006.01) |
| C12P 19/18 | (2006.01) |
| B01D 61/02 | (2006.01) |
| B01D 61/58 | (2006.01) |
| C07H 13/02 | (2006.01) |

(52) U.S. Cl.
CPC .............. *C07H 1/08* (2013.01); *A23L 33/195* (2016.08); *B01D 15/362* (2013.01); *B01D 15/363* (2013.01); *B01D 61/027* (2013.01); *B01D 61/142* (2013.01); *B01D 61/145* (2013.01); *B01D 61/16* (2013.01); *B01D 61/58* (2013.01); *C07H 1/06* (2013.01); *C07H 13/02* (2013.01); *C07H 13/04* (2013.01); *C07H 23/00* (2013.01); *C08B 37/0003* (2013.01); *C12P 19/04* (2013.01); *C12P 19/18* (2013.01); *C12Y 204/99* (2013.01); *B01D 2311/06* (2013.01); *B01D 2311/2623* (2013.01); *B01D 2311/2626* (2013.01); *B01D 2311/2688* (2013.01); *B01D 2317/025* (2013.01)

(58) Field of Classification Search
None
See application file for complete search history.

(56) References Cited

U.S. PATENT DOCUMENTS

| | | | |
|---|---|---|---|
| 5,575,916 | A | 11/1996 | Berry et al. |
| 2002/0034805 | A1 | 3/2002 | Gilbert et al. |
| 2002/0148791 | A1 | 10/2002 | Defrees |
| 2004/0072306 | A1* | 4/2004 | Baldenius .............. C12P 13/02 435/106 |
| 2005/0003499 | A1 | 6/2005 | Keri et al. |
| 2007/0020736 | A1 | 1/2007 | Samain |
| 2008/0145899 | A1 | 6/2008 | Johnson et al. |
| 2012/0208181 | A1* | 8/2012 | Merighi .................. C12N 9/00 435/6.1 |
| 2016/0302436 | A1* | 10/2016 | Huumonen .......... A23C 9/1307 |

FOREIGN PATENT DOCUMENTS

| | | |
|---|---|---|
| CN | 102154163 | 8/2011 |
| EP | 1911850 A1 | 4/2008 |
| EP | 2408794 B1 | 5/2013 |
| WO | 9614124 A1 | 5/1996 |
| WO | 96/32492 | 10/1996 |
| WO | 98/15581 | 4/1998 |
| WO | 99//31224 | 6/1999 |
| WO | 01/04341 A1 | 1/2001 |

(Continued)

OTHER PUBLICATIONS

Dowex 22, retrieved on Oct. 2019 from https://www.dupont.com/content/dam/dupont/amer/us/en/products/water-solutions/documents/177-01681.pdf (Year: 2019).*

Mitsubishi Chemical Corporation. (2013) Product Line Brochure DIAION [Brochure], 10 pages.

AG® 1-X8 Anion Exchange Resin, analytical grade, 100-200 mesh, chloride form, 500 g #1401441. Retrieved on Jan. 18, 2019, from URL: http://www.bio-rad.com/en-us/sku/1401441-ag-1-x8-anion-exchange-resin-analytical-grade-100-ndash-200-mesh-chloride-form-500-g?ID=1401441 (2 pages).

(Continued)

*Primary Examiner* — Dale R Miller
(74) *Attorney, Agent, or Firm* — Neal, Gerber & Eisenberg LLP

(57) ABSTRACT

The present invention relates to a method for separating sialylated oligosaccharides from a fermentation broth in which they are produced by a genetically modified microorganism The separation comprises the steps of: i) ultrafiltration; ii) nano-filtration; iii) optionally, activated charcoal treatment; and iv) treatment with strong anion and/or cation exchange resin.

20 Claims, No Drawings

(56) References Cited

FOREIGN PATENT DOCUMENTS

| | | | |
|---|---|---|---|
| WO | 2006/029538 A1 | 3/2006 | |
| WO | 2006/034225 A2 | 3/2006 | |
| WO | 2007/056191 A2 | 5/2007 | |
| WO | 2007/101862 A1 | 9/2007 | |
| WO | 2009/113861 A2 | 9/2009 | |
| WO | 2010106320 A2 | 9/2010 | |
| WO | 2010/116317 A1 | 10/2010 | |
| WO | 2011/100979 A1 | 8/2011 | |
| WO | 2012/007588 A9 | 1/2012 | |
| WO | 2013/182206 A1 | 12/2013 | |
| WO | 2014/048439 A1 | 4/2014 | |
| WO | 2014/153253 A1 | 9/2014 | |
| WO | 2015106943 A1 | 7/2015 | |
| WO | 2015/188834 A1 | 12/2015 | |
| WO | 2017/101958 A1 | 6/2017 | |
| WO | 2017152918 A1 | 9/2017 | |
| WO | 2019043029 A1 | 3/2019 | |

OTHER PUBLICATIONS

Antoine, T. et al., "Highly Efficient Biosynthesis of the Oligosaccharide Moiety of the GD3 Ganglioside by Using Metabolically Engineered *Escherichia coli*," Angew. Chem. Int. Ed., 2005, vol. 44, pp. 1350-1352.

Chen, X. (2015)."Human Milk Oligosaccharides (HMOS): Structure, Function, and Enzyme-Catalyzed Synthesis," Elsevier Inc. (vol. 72), Advances in Carbohydrate Chemistry and Biochemistry, pp. 113-190. http://dx.doi.org/10.1016/bs.accb.2015.08.002.

Drouillard, S. et al., "Efficient synthesis of 6'-sialyllactose, 6'6-disialyllactose, and 6'-KDO-lactose by metabolically engineered *E. coli* expressing a multifunctional sialyltransferase from the *Photobacterium* sp. JT-ISH-224," Carbohydrate Research, 2010, vol. 345, pp. 1394-1399.

Fierfort, N. et al., "Genetic engineering of *Escherichia coli* for the economical production of sialylated oligosaccharides," Journal of Biotechnology, 2008, vol. 134, pp. 261-265.

Fort, S. et al., "Biosynthesis of conjugatable saccharidic moieties of GM2 and GM3 gangliosides by engineered *E. coli*," Chem. Commun., 2005, pp. 2558-2560.

Gilbert, M. et al., "The synthesis of sialylated oligosaccharides using a CMP-Neu5Ac synthetase/sialyltransferase fusion," Nature Biotechnology, 1998, vol. 16, pp. 769-772.

International Search Report and Written Opinion dated Mar. 31, 2017 for International Patent Application No. PCT/DK2017/050063 filed on Mar. 7, 2016.

Maru, I. et al., "Synthesis of Sialyllactose from N-Acetylneuraminic Acid and Lactose by a Neuraminidase from Arthrobacter ureafaciens," Biosi. Biotech. Biochem., 1992, vol. 56(10), pp. 1557-1561.

Masuda, M. et al., "Continuous Production of Sialyllactose from Colominic Acid Using a Membrane Reactor," Journal of Bioscience and Bioengineering, 2000, vol. 89(2), pp. 119-125.

Mine, T. et al., "An alpha-2,3-Sialyltransferase from *Photobacterium* sp. JT-ISH-224 Transfers N-Acetylneuraminic Acid to Both the O-2 and O-3' Hydroxyl Groups of Lactose," Journal of Carbohydrate Chemistry, 2010, vol. 29(2), pp. 51-60.

Priem, B. et al., "A new fermentation process allows large-scale production of human milk oligosaccharides by metabolically engineered bacteria," Glycobiology, 2002, vol. 12(4), pp. 235-240.

Ten Bruggencate, S.J. et al., Functional role and mechanisms of sialyllactose and other sialylated milk oligosaccharides, Nutrition Reviews, 2014, vol. 72(6), pp. 377-389.

Urashima, T. et al. (2011) Nutrition and Diet Research Progress: Milk Oligosaccharides. New York: Nova Science Publishers, Inc, 92 pages.

Phillips, T., "Enzymes Used in the Dairy Industry," The Balance, May 14, 2019 [retrieved on Sep. 12, 2019].

\* cited by examiner

SEPARATION OF OLIGOSACCHARIDES FROM FERMENTATION BROTH

CROSS-REFERENCE TO RELATED APPLICATION

This application is a national stage entry pursuant to 35 U.S.C. § 371 of International Application No. PCT/DK2017/050063, filed on Mar. 7, 2017, which claims priority to DK Patent Application No. PA 2016 70131, filed on Mar. 7, 2016, the contents of all of which are fully incorporated herein by reference.

FIELD OF THE INVENTION

The present invention relates to the isolation and purification of sialylated oligosaccharides from a fermentation broth in which they are produced by a microorganism.

BACKGROUND OF THE INVENTION

During the past decades, the interest in the preparation and commercialisation of human milk oligosaccharides (HMOs) has been increasing steadily. The importance of human milk oligosaccharides is directly linked to their unique biological activities. Sialylated human milk oligosaccharides such as disialyllacto-N-tetraose, 3'-O-sialyl-3-O-fucosyllactose, 6'-O-sialyllactose, 3'-O-sialyllactose, 6'-O-sialylated-lacto-N-neotetraose and 3'-O-sialylated-lacto-N-tetraose, are among the major components of human milk. In these sialylated human milk oligosaccharides the sialic acid residue is always linked to the 3-O- and/or 6-O-position of a terminal D-galactose or to the 6-O-position of a non-terminal GlcNAc residue via α-glycosidic linkages. Sialylated HMOs are thought to have significant health benefits for the neonate, because of their roles in supporting resistance to pathogens, gut maturation, immune function and cognitive development (ten Bruggencate et al. *Nutr. Rev.* 72, 377 (2014)).

Efforts to develop processes for synthesizing HMOs, including sialylated HMOs, have increased significantly in the last ten years due to their roles in numerous human biological processes. In this regard, processes have been developed for producing them by microbial fermentations, enzymatic processes, chemical syntheses, or combinations of these technologies. With regard to productivity, fermentation processes, on a lab scale, to produce 3'-SL and 6'-SL have proved to be promising.

However, to isolate sialylated lactoses or sialylated oligosaccharides from a complex matrix such as a fermentation broth is a challenging task. Antoine et al. *Angew. Chem. Int. Ed.* 44, 1350 (2005) and US 2007/0020736 disclosed the production of 3'-SL and accompanying di- and trisialylated lactoses by a genetically modified *E. coli*; the broth containing approx. 0.8 mM 3'-SL was treated as follows: adsorption of the products from the centrifuged supernatant on charcoal/celite, washing away the water soluble salts with distilled water, eluting the compounds by gradient aqueous ethanol, separation of the sialylated products on a Biogel column and desalting, leading to 49 mg of 3'-SL from 1 litre of broth. WO 01/04341 and Priem et al. *Glycobiology* 12, 235 (2002) disclosed the production of 3'-SL by a genetically modified *E. coli*; 3'-SL was isolated by the following sequence of operations: heat permeabilization of the producing cells followed by centrifugation, adsorption of the product from the supernatant on charcoal/celite, washing away the water soluble salts with distilled water, eluting the compound by gradient aqueous ethanol, binding the compound to a strong anion exchanger in $HCO_3^-$-form, elution of the compound with a linear gradient $NaHCO_3$-solution, then eliminating the sodium bicarbonate with a cation exchanger (in $H^+$-form), resulting in isolated 3'-SL with 49% purification yield. WO 2007/101862 and Fierfort et al. *J. Biotechnol.* 134, 261 (2008) disclosed an alternative workup procedure of a 3'-SL fermentation broth, the procedure comprising the steps of heat permeabilization of the producing cell, centrifugation, adjusting the pH of the extracellular to 3.0 by the addition of a strong cation exchanger resin in acid form, removal of the precipitated proteins by centrifugation, adjusting the pH of the supernatant to 6.0 by the addition of a weak anion exchanger in base form, binding the sialyllactose to an anion exchanger in $HCO_3^-$-form, after washing with distilled water, elution of the compound with a continuous gradient $NaHCO_3$-solution, eliminating the sodium bicarbonate with a cation exchanger (in $H^+$-form) until pH 3.0 was reached, then adjustment of the pH to 6.0 with NaOH. The above purification allowed to isolate 15 g of 3'-SL from 1 litre of broth containing 25.5 g of 3'-SL. Drouillard et al. *Carbohydr. Res.* 345, 1394 (2010)) applied Fierfort's procedure above to a fermentation broth containing 6'-SL (11 g/l) and some 6,6'-disialyllactose (DSL), and thus isolated 3.34 g 6'-SL +DSL in a ratio of 155/86.

WO 2006/034225 describes two alternative purifications of 3'-SL from a producing fermentation broth. According to the first procedure, the lysate from the culture was diluted with distilled water and stirred with activated charcoal/celite. The slurry was washed with water, then the product was eluted from the charcoal/celite with aq. ethanol. According to the second method, the culture cells were heat treated and the precipitated solids were separated from the supernatant by centrifugation. The resulting supernatant was processed through a microfilter, the permeate was passed through a 10 kDa membrane, then nanofiltered. The resulting retentate was then diafiltered to collect the final sample. Both purification methods provided 90-100 mg 3'-SL from 1 litre of fermentation broth.

The drawback of the above sialyllactose purification processes from a fermentation culture is the poor to moderate purification yield. Thus simpler and/or more effective ways for isolating and purifying these products from fermentation broths on an industrial scale have been sought.

SUMMARY OF THE INVENTION

The invention relates to a method obtaining a sialylated oligosaccharide from a fermentation broth, wherein said sialylated oligosaccharide is produced by culturing a genetically modified microorganism capable of producing said sialylated oligosaccharide from an internalized carbohydrate precursor, comprising the steps of:

i) ultrafiltration (UF), preferably to separate biomass from the broth, ii) nanofiltration (NF), preferably to concentrate the sialylated oligosaccharide in the broth and/or reduce an inorganic salt content of the broth, iii) optional activated charcoal treatment, preferably to decolorize the broth, and iv) treating the broth with a strong anion exchange resin and/or cation exchange resin, preferably to remove charged materials.

Preferably, step i) is performed before any of the steps ii), iii) and iv). Steps ii), iii) and iv) can be conducted in any order. The sialylated oligosaccharide can be collected after any of the steps ii), iii) and iv).

Also preferably, the method is carried out in the following sequence: step i), step ii), optional step iii) and step iv).

One embodiment the invention relates to a method for isolating a sialylated oligosaccharide from a fermentation broth, wherein said sialylated oligosaccharide is produced by culturing a genetically modified microorganism capable of producing said sialylated oligosaccharide from an internalized carbohydrate precursor, comprising the steps of:
i) ultrafiltration (UF) of the fermentation broth and collecting the UF permeate (UFP),
ii) nanofiltration (NF) of the UFP and collecting the NF retentate (NFR),
iii) optionally, treating the UFP and/or NFR with activated charcoal, and collecting the charcoal eluate (CE), and
iv) treating the UFP, NFR and/or CE with a strong anion exchange resin and/or cation exchange resin.

The steps iii) and iv) can be conducted in any order.

DETAILED DESCRIPTION OF THE INVENTION

1. Terms and Definitions

In accordance with this invention, the term "sialylated oligosaccharide" preferably means a sugar polymer containing at least two monosaccharide units, at least one of which is a sialyl (N-acetylneuraminyl) moiety. The sialylated oligosaccharide can have a linear or branched structure containing monosaccharide units that are linked to each other by interglycosidic linkage. Advantageously, the sialylated oligosaccharide is an acidic human milk oligosaccharide.

The term "acidic human milk oligosaccharide" or "acidic HMO" preferably means a complex carbohydrate found in human breast milk (Urashima et al.: *Milk Oligosaccharides*. Nova Science Publishers, 2011) comprising a core structure being a lactose unit at the reducing end that can be elongated by one or more β-N-acetyl-lactosaminyl and/or one or more β-lacto-N-biosyl units, and which core structure is substituted by an α-N-acetyl-neuraminyl (sialyl) moiety and optionally can be substituted by an α L-fucopyranosyl moiety. In this regard, the acidic HMOs have at least one sialyl residue in their structure. Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DS-LNT).

The term "genetically modified cell" or "genetically modified microorganism" preferably means a cell of a microorganism, such as a bacterial cell, e.g. an *E. coli* cell, in which there is at least one alteration in its DNA sequence. The alteration can result in a change in the original characteristics of the wild type cell, e.g. the modified cell is able to perform additional chemical transformation due to the introduced new genetic material that encodes the expression of an enzymes not being in the wild type cell, or is not able to carry out transformation like degradation due to removal of gene/genes (knockout). A genetically modified cell can be produced in a conventional manner by genetic engineering techniques that are well-known to those skilled in the art.

The term "genetically modified microorganism capable of producing a sialylated oligosaccharide from an internalized carbohydrate precursor" preferably means a cell of a microorganism which is genetically manipulated (vide supra) to comprise a recombinant gene encoding a sialyl transferase necessary for the synthesis of said sialylated oligosaccharide, a biosynthetic pathway to produce a sialic acid nucleotide donor suitable to be transferred by said glycosyl transferase to a carbohydrate precursor (acceptor) and a mechanism of internalization of a carbohydrate precursor (acceptor) from the culture medium into the cell where it is sialylated to produce the sialylated oligosaccharide of interest.

The term "around" means, in one embodiment, ±10% deviation from the value indicated, or in another embodiment, ±5% deviation.

2. Method for Separating Sialylated Oligosaccharides

The invention relates to a method for separating a sialylated oligosaccharide/sialylated lactose from other compounds present in a fermentation broth obtained by culturing a genetically modified microorganism capable of producing said sialylated oligosaccharide/sialylated lactose from an internalized carbohydrate precursor.

The method comprises the following separation steps in any order:
i) ultrafiltration (UF),
ii) nanofiltration (NF),
iii) optionally, activated charcoal treatment, and
iv) treatment with strong anion and/or cation exchange resin.

In one preferred embodiment, the method comprises:
i) ultrafiltration (UF) of the fermentation broth and collecting the ultrafiltration permeate (UFP),
ii) nanofiltration (NF) of the UFP and collecting the nanofiltration retentate (NFR),
iii) optionally, activated charcoal treatment of UFP and/or NFR, and collecting the charcoal eluate (CE), and
iv) treatment of UFP, NFR and/or CE of (a) with a strong anion and/or cation exchange resin.

In another preferred embodiment, the method comprises:
i) ultrafiltration (UF) of the fermentation broth and collecting the ultrafiltration permeate (UFP),
ii) nanofiltration (NF) of the UFP and collecting the nanofiltration retentate (NFR),
iii) treatment of UFP and/or NFR with strong anion and/or cation exchange resin, and collecting the resin eluate (RE), and
iv) optionally, activated charcoal treatment of UFP, NFR and/or RE and collecting the charcoal retentate.

The method of the invention provides a solution highly enriched with the sialylated oligosaccharide/sialylated lactose from which the sialylated oligosaccharide/sialylated lactose can be obtained in high yield and preferably with a satisfactory purity.

2.1. Production of the Sialylated Oligosaccharide by a Genetically Modified Microorganism The production of the sialylated oligosaccharide/sialylated lactose by culturing a genetically modified cell preferably occurs in the following way. An exogenously added acceptor is internalized from the culture medium into the cell where it is converted to the sialyl oligosaccharide of interest in a reaction comprising enzymatic sialylation. In one embodiment, the internalization can take place via a passive transport mechanism during which the exogenous acceptor diffuses passively across the plasma membrane of the cell. The flow is directed by the concentration difference in the extra- and intracellular space with respect to the acceptor molecule to be internalized, which acceptor is supposed to pass from the place of higher concentration to the zone of lower concentration tending towards equilibrium. In another embodiment, the exogenous acceptor can be internalized in the cell with the aid of an active transport mechanism, during which the exogenous acceptor diffuses across the plasma membrane of the cell under the influence of a transporter protein or permease of the cell. Lactose permease (LacY) has specificity towards mono- or disaccharide selected from galactose, N-acetyl-glucosamine, a galactosylated monosaccharide (such as lactose), an N-acetyl-glucosaminylated monosaccharide and glycosidic derivatives thereof. All these carbohydrate derivatives can be easily taken up by a cell having a LacY permease by means of an active transport and accumulate in the cell before being glycosylated (WO 01/04341, Fort et al. *J. Chem. Soc., Chem. Comm.* 2558 (2005), EP-A-1911850, WO 2013/182206, WO 2014/048439). This is because the cell is able to transport these carbohydrate acceptors into the cell using its LacY permease, and the cell lacks any enzymes that could degrade these acceptors, especially LacZ. The specificity towards the sugar moiety of the substrate to be internalized can be altered by mutation by means of known recombinant DNA techniques. In a preferred embodiment, the exogenously added acceptor is lactose, and its internalization takes place via an active transport mechanism mediated by a lactose permease of the cell, more preferably LacY. Being internalized in the cell, the acceptor is sialylated by means of a sialyl transferase expressed by a heterologous gene or nucleic acid sequence which is introduced into the cell by known techniques, e.g. by integrating it into the chromosome of the cell or using an expression vector. The genetically modified cell comprises a biosynthetic pathway to produce a sialic acid monosaccharide nucleotide donor (typically CMP-sialic acid) suitable to be transferred by the corresponding sialyl transferase. The genetically modified cell can produce CMP-sialic acid, in two ways. In one way, exogenously added sialic acid is internalized actively or passively, preferably actively by a sialic acid permease, more preferably by that encoded by nanT, and subsequently converted to CMP-sialic acid by a CMP-NeuAc synthase, e.g. encoded by a heterologous neuA. In another way the internally available UDP-GlcNAc is utilized, by expressing heterologous neuC, neuB and neuA that convert it to CMP-sialic acid via ManNAc and sialic acid as intermediates. In the meantime, the cell's catabolic activity on sialic acid and its precursor is suppressed by inactivating/deletion of the aldolase gene (nanA) and/or the ManNAc kinase gene (nanK). The internalized carbohydrate precursor can be the subject of glycosylation other than sialylation, e.g. N-acetyl-glucosaminylation, galactosylation and/or fucosylation before being sialylated as described above.

2.2. Step i) of the Separation of the Sialylated Oligosaccharide

According to step i) of the method, the broth obtained from fermentation is subjected to ultrafiltration, preferably as a first step. The fermentation broth typically contains, besides the sialylated oligosaccharide/sialylated lactose produced, the biomass of the cells of the used microorganism together with proteins, protein fragments, DNA, endotoxins, biogenic amines, inorganic salts, unreacted carbohydrate acceptor such as lactose, sugar-like by-products, sialic acid, colorizing bodies, etc. The ultrafiltration step is to separate the biomass and, preferably, also high molecular weight suspended solids from the soluble components of the broth which pass through the ultrafiltration membrane in the permeate. This UF permeate (UFP) is an aqueous solution containing the produced sialylated oligosaccharide/sialylated lactose.

Any conventional ultrafiltration membrane can be used having a molecular weight cut-off (MWCO) range between about 1 and about 500 kDa, such as 10-250, 50-100, 200-500, 100-250, 1-100, 1-50, 10-25, 1-5 kDa, any other suitable sub-ranges. The membrane material can be a ceramic or made of a synthetic or natural polymer, e.g. polysulfone, polypropylene, cellulose acetate or polylactic acid. The ultrafiltration step can be applied in dead-end or cross-flow mode. This step i) may comprise more than one ultrafiltration step using membranes with different MWCO, e.g. using two ultrafiltration separations wherein the first membrane has a higher MWCO than that of the second membrane. This arrangement may provide a better separation efficacy of the higher molecular weight components of the broth. After this separation step the permeate contains materials that have a molecular weight lower than the MWCO of the second membrane, including the sialylated oligosaccharide/sialylated lactose of interest.

In one embodiment, the fermentation broth is ultrafiltered using a membrane having a MWCO of 5-30 kDa, such as 10-25, 15 or 20 kDa.

Preferably, the pH of the fermentation broth processed in the UF step is adjusted to around 4-5.5, e.g. around 5. This pH range offers a better performance of the UF step and higher recovery yield of the sialylated oligosaccharide/sialylated lactose, like sialylated lactoses, as it prevents the rearrangement to the corresponding fructose isomers in particular when the UF is performed at elevated temperature (vide infra), and in addition prevents inorganic precipitation during concentration.

In one embodiment, the ultrafiltration step is preceded by diluting the fermentation broth. The UF step is conducted so that the degree of concentration (concentration factor, $CF_1$) is at least 1.25, more preferably at least 1.5. On the other hand, the $CF_1$ is advantageously not more than 4, preferably not more than 3. The concentration factor ($CF_1$) in this UF step is the ratio of the volume (or mass) of the feed (which equals to that of the diluted broth) and that of the UF retentate (UFR). For example, when 50 kg of broth is diluted to 100 kg, which diluted broth is ultrafiltered, and 40 kg of permeate and 60 kg of retentate are collected, the $CF_1$ is 1.67. Exemplary $CF_1$ ranges of the UF step are 1.25-4, 1.25-3, 1.25-2.25, 1.5-4, 1.5-3, 1.5-2.25, 1.25-2 or 1.5-2. The UFR can be optionally washed with small amounts of water. In general, this UF step comprising a dilution of the broth prior to ultrafiltartion and optionally washing the UFP with water is characterized with dilution factor ($DF_1$) of 1-3.5. The $DF_1$ in this step is calculated as the ratio of the total volume (or mass) of the UFP optionally combined with washing filtrate and that of the fermentation broth undiluted. For example, when 50 kg of broth is diluted to 100 kg, which diluted broth is ultrafiltered, and 70 kg of UFP and 30 kg UFR is collected, then the $DF_1$ is 1.4. Exemplary $DF_1$ ranges are 1-3.1, 1.5-3.1, 1.8-3.1, 1-2.5, 1.5-2.5, 1.8-2.5, 2-3.1, 2-2.5, 2-2.3.

In other embodiment, the fermentation broth as obtained (that is non-diluted) is ultrafiltered, the UF step is conducted so that the degree of concentration (concentration factor, $CF_2$) is at least 1.25, more preferably at least 1.5. On the other hand, the $CF_2$ is advantageously not more than 4, preferably not more than 3. The concentration factor in this UF step is the ratio of the volume (or mass) of the broth (which equals to that of the UF feed) and that of the UF retentate (UFR). For example, when 100 kg of broth is directly ultrafiltered and 40 kg of permeate and 60 kg of retentate are collected, the $CF_2$ is 1.67. Exemplary $CF_2$ ranges of the UF step are 1.25-4, 1.25-3, 1.25-2.25, 1.5-4, 1.5-3, 1.5-2.25, 1.25-2 or 1.5-2. Preferably, this step comprises a washing step of the UFR obtained in the UF step above, in order to improve the recovery yield of the sialylated oligosaccharide/sialylated lactose product. This step is performed by adding water, preferably purified water, to the UFR to give a suspension and the aqueous phase of the suspension is passed through the same UF membrane used in the above UF step to collect a washing filtrate of preferably the same volume (or mass) as that of the washing water applied. As a general rule, the higher the CF of the precedent UF step, the more the water added. In addition, the more the washing water, the more the additionally recovered product. However, above a certain volume of washing water no significantly more product can be washed out from the UFR. The washing water can be added in one portion or more subsequent portions, however it is favourable when the washing water is added continuously to the UFR with the same flow rate as the flow rate of the filtrate collection, to maintain a constant UFR concentrate volume. After the washing step, the UFP and the washing filtrate are combined for the next purification/isolation step(s). The combined UFP+ washing filtrate fractions contain 85-96% of the sialylated oligosaccharide/sialylated lactose product of the fermentation broth (by mass), when their dilution factor ($DF_2$) is 1 to 3.5. $DF_2$ in this step is calculated as the ratio of the total volume (or mass) of the UFP combined with washing filtrate and that of the undiluted fermentation broth (that equals to that of the UF feed). For example, when 100 kg of broth is directly ultrafiltered, 40 kg of UFP is collected, and the UFR is washed with 200 kg of water, then the $DF_2$ is 2.4. Exemplary $DF_2$ ranges are 1-3.1, 1.5-3.1, 1.8-3.1, 1-2.5, 1.5-2.5, 1.8-2.5, 2-3.1, 2-2.5, 2-2.3. Preferably, the application of more than 3-fold washing water volume or washing water mass (compared to the broth volume or mass before UF) does not significantly contribute to improving the recovery. On the other hand, the collection of higher volume of washing filtrate increases the technological time of the subsequent steps ii), iii) and iv). From technological point of view it is advantageous, when the volume (or mass) of the washing water used is around 1.5-2.5-fold, e.g. 1.6-1.9-fold, of that of the broth used in the UF step.

The UF step is, or the UF and washing steps are, conducted at constant temperature, preferably between 15 and 65° C., such as e.g. at 15-20 or at 55-65° C. Throughout this range a satisfactory recovery yield is available, however the higher the temperature, the higher the recovery yield. As a consequence, at higher temperature lower DF is sufficient to reach the same recovery yield. Preferably, at 55-65° C. a DF of around 2.0-2.3 ensures around 90% of recovery yield or even higher.

It should be emphasized that no heat deactivation and disruption of the producing cell, or treating the cell with an agent (like Triton X) that make the cell wall more permeable, is necessary to apply in order to collect the intracellularly accumulated product.

2.3. Step ii) of the Separation of the Sialylated Oligosaccharide

Step ii) of the method comprises a nanofiltration (NF) step. Step ii) may follow step i), optional step iii) or step iv). This nanofiltration step may advantageously be used to concentrate the previously treated fermentation broth containing the sialylated oligosaccharide/sialylated lactose and/ or to remove ions, mainly monovalent ions, and organic materials having a molecular weight lower than that of the sialylated oligosaccharide\sialylated lactose, such as monosaccharides. The nanofiltration membrane has a MWCO that ensures the retention of the sialylated oligosaccharide\sialylated lactose of interest, that is its MWCO is lower than that of the ultrafiltration membrane(s) used in step a), and around 25-50% of the molecular weight of the sialylated oligosaccharide/sialylated lactose. As an example, a nanofiltration membrane having a MWCO of about 150-300 Da is suitable for retaining sialylated lactose. In this regard the sialylated oligosaccharide/sialylated lactose is accumulated in the NF retentate (NFR). The nanofiltration can be combined with diafiltration with water in order to remove permeable molecules more effectively, e.g. until the conductivity of the permeate showing no or very low presence of salts.

The NF step according to this invention is conducted, with or without the optional diafiltration step, at constant temperature, preferably between 15-45° C., such as at 15-20° C. or at 35-45° C. This NF step, with or without diafiltration, is continued until reaching the desired concentration of the sialylated oligosaccharide\sialylated lactose in the NFR. Other technical parameters like setting in the flux and pressure is a matter of routine skills.

With the above disclosed NF step, at least 95% of the sialylated oligosaccharide/sialylated lactose obtained in the previous step can be retained.

In one preferred embodiment, step ii) follows step i), that is the UF permeate obtained in step i) is nanofiltered and the NF retentate containing the produced sialylated oligosaccharide/sialylated lactose is collected and subjected either further separation steps of the method or used as source solution for obtaining the sialylated oligosaccharide/sialylated lactose.

2.4. Step iii) of the Separation of the Sialylated Oligosaccharide

The method, as mentioned above, may comprise one or more optional separation steps, such as step iii) described below.

According to one embodiment, the method comprises the optional step iii): an active charcoal treatment is applied. Optional step iii) may follow step i), step ii) or step iv). The active charcoal (AC) treatment helps to remove colorizing agents and/or water soluble contaminants, such as salts, if required.

A carbohydrate substance like a sialylated oligosaccharide/sialylated lactose of interest tends to be bound to the surface of charcoal particles from its aqueous solution, e.g. an aqueous solution obtained after on step i), step ii) or step iv). Similarly, the colorizing agents also adsorb to the charcoal. While the carbohydrates and colour giving materials are adsorbed, water soluble materials not or weaker bound to the charcoal can be eluted with water. Changing the eluent from water to aqueous ethanol the adsorbed sialylated oligosaccharide/sialylated lactose can be easily eluted and collected in a separate fraction. The adsorbed colour giving substances would still remain adsorbed on the charcoal, thus decolourization and desalination can be achieved simultaneously in step iii). The charcoal treatment can be conducted by adding charcoal (e.g. powder, pellet or granulate) to the aqueous solution of the sialylated oligosaccharide/sialylated lactose under stirring, filtering off the charcoal, re-suspending in aqueous ethanol under stirring and separating the charcoal by filtration. In higher scale purification, the aqueous solution of the sialylated oligosaccharide/sialylated lactose after step i), step ii) or step iv) is loaded to a column packed with charcoal, which may optionally be mixed with celite, then the column is washed with the required eluent. The fractions containing the sialylated oligosaccharide/ sialylated lactose are collected. From these fractions, if necessary, the ethanol may be removed by e.g. evaporation to give an aqueous solution of the sialylated oligosaccharide/ sialylated lactose.

Alternatively, under certain conditions, the sialylated oligosaccharide is not, or at least not substantially, adsorbed on the charcoal particles and elution with water gives rise to an aqueous solution of the sialylated oligosaccharide/sialylated lactose without its significant loss, meanwhile the colour giving substances remain adsorbed. To achieve this, the amount of activated charcoal applied for decolourization should be about 12-25% by mass relative to the sialylated oligosaccharide content of the feed solution obtained in a previous step, preferably about 15-20% relative to the sialyl lactose content of the feed solution. With this particular arrangement as much as at least 90% of the sialylated oligosaccharide/sialylated lactose (by mass) obtained in the previous step can be collected back in the form of a decolourized solution.

Optionally, the charcoal bed can be washed with pure water to collect further amounts of sialylated oligosaccharide/sialylated lactose which is optionally bound to charcoal. The more the washing water applied, the more the additionally recovered product. However, above a certain volume of washing water no significantly more product can be washed out from the charcoal, and the chance of washing down already bound colour bodies is increasing. Therefore, to keep a trade-off between a maximum recovery yield and the dilution of the eluate, 16-25 l purified water/kg of charcoal is used in this washing step, preferably in at least two portions. This results in recovering further around 5% of sialylated oligosaccharide/sialylated lactose from charcoal (thus to reach at least 95% of accumulated recovery yield in this AC treatment step), whereas the obtained solution is colourless and the AC dilution factor is only around 1.4-1.9 (the AC dilution factor is calculated as the ratio of the volume (or mass) of charcoal treated combined eluents and that of feed solution). In one preferred embodiment, the active charcoal treatment is following the nanofiltration step ii), and is applied on the NF retentate.

2.5. Step iv) of the Separation of the Sialylated Oligosaccharide

In step iv), the pre-treated aqueous solution of the sialylated oligosaccharide/sialylated lactose from step i), ii) or iii) is further purified by means of an ion exchange resin.

According to one embodiment of step iv), the ion exchange resin is an anion exchange resin, preferably a strong anion exchange resin. The aqueous solution of the sialylated oligosaccharide/sialylated lactose is contacted with an anion exchange resin in any suitable manner which would allow the negatively charged materials to be absorbed onto the anion exchange resin, including the sialylated oligosaccharide/sialylated lactose. The resulting liquid, after contacting with the anion exchange resin as eluate, contains primarily water, cations and neutral carbohydrates like the carbohydrate acceptor previously added to the fermentation culture to be sialylated, e.g. lactose (if still left after one or more previous purification steps). The sialylated oligosaccharide/sialylated lactose can be recovered from the anion exchange resin by eluting it with an aqueous solution of a suitable salt such as that of an alkali metal (Li, Na, K), alkaline earth metal (such as Ca, Mg) or ammonium ion in the form of e.g. acetate, halide (such as chloride or bromide), carbonate, bicarbonate, sulfate, etc., as an eluent. Alternatively, the retained sialylated oligosaccharide/sialylated lactose can also be removed from the anion exchange resin with an aqueous alkali solution to obtain its corresponding salt. In order to get the sialylated oligosaccharide/sialylated lactose in acidic form, an acid solution as eluent can be used, e.g. HCl, sulfuric acid, nitric acid, etc. The concentration of the aqueous alkali or acidic solution must be dilute enough so as not to destroy the structure of the sialylated oligosaccharide/sialylated lactose. Suitable desorbing conditions can be determined through routine experimentation. If necessary, the sialylated oligosaccharide/sialylated lactose in acidic form can be converted into its organic or inorganic salt as described e.g. in WO 2011/100979. Either the acidic sialylated oligosaccharide/sialylated lactose or its suitable salt can be isolated from its aqueous solution by precipitation using an alcohol or aqueous alcohol solution.

According to another embodiment of step iv), the ion exchange resin is a cation exchange resin, preferably a strong cation exchange resin. The solution of the sialylated oligosaccharide/sialylated lactose is contacted with the cation exchange resin in any suitable manner which would allow positively charged materials to be absorbed onto the cation exchange resin. The resulting liquid (eluate), after contacting with the cation exchange resin, contains the sialylated oligosaccharide/sialylated lactose in acidic form (when the cation exchange resin is in H-form) or a salt form (when the cation exchange resin is in the corresponding salt form). If necessary, the sialylated oligosaccharide/sialylated lactose in acidic form can be converted into its organic or inorganic salt as described e.g. in WO 2011/100979. Preferably, an aqueous alkali solution is used until pH reaches around 7 to obtain the corresponding alkali salt of the sialylated oligosaccharide/sialylated lactose. Either the acidic sialylated oligosaccharide/sialylated lactose or its suitable salt can be isolated from its aqueous solution by precipitation using an alcohol or an aqueous alcohol solution.

In step iv), the concentration of the aqueous alkali or the acid solution optionally used as eluent must be diluted enough so as not to not degrade the sialylated oligosaccharide/sialylated lactose.

One of the ion exchange resin treatments disclosed above in step iv) may be sufficient to obtain the sialylated oligosaccharide/sialylated lactose in a required purity. If necessary, both cation and anion exchange resin chromatography, in any order, can be applied.

Also in step iv), the degree of crosslinking in the ion exchange resin can be chosen depending on the operating conditions of the ion exchange column. A highly crosslinked resin offers the advantage of durability and a high degree of mechanical integrity, however suffers from a decreased porosity and a drop off in mass-transfer. A low-crosslinked resin is more fragile and tends to swell by absorption of mobile phase. The particle size of the ion exchange resin is selected to allow an efficient flow of the eluent, while the charged materials are still effectively removed. A suitable flow rate may also be obtained by applying a negative pressure to the eluting end of the column or a positive pressure to the loading end of the column, and collecting the eluent. A combination of both positive and negative pressure may also be used.

Non-limiting examples of a suitable acidic cation exchange resin can be e.g. Amberlite IR100, Amberlite IR120, Amberlite FPC22, Dowex 50WX, Finex CS16GC, Finex CS13GC, Finex CS12GC, Finex CS11GC, Lewatit S, Diaion SK, Diaion UBK, Amberjet 1000, Amberjet 1200.

Non-limiting examples of a suitable basic anion exchange resin can be e.g. Amberjet 4200, Amberjet 4600, Amberlite IR400, Amberlite IR410, Amberlite IR458, Diaion SA, Diaion UBA120, Lewatit MonoPlus M, Lewatit S7468.

In one embodiment, a strong cation exchange resin in $H^+$-form is used in step iv) followed by addition of an alkaline solution to the eluent to obtain an alkaline salt of the sialylated oligosaccharide.

In other embodiment, step iv) of the present invention comprises the utilization of a strong cation exchange resin in salt form, more preferably the salt form is of a monovalent alkaline cation such as $Na^+$ or $K^+$. With this type of ion exchange resin, cations of the load solution containing the sialylated oligosaccharide/sialylated lactose are exchanged by the alkaline cation (e.g. $Na^+$ or $K^+$) of the resin directly to provide the corresponding alkaline salt of the sialylated oligosaccharide/sialylated lactose without the need of pH-adjustment suggested by the prior art.

The recovery yield of this step is more than 95%, even near to quantitative. Excess of the monovalent alkaline cations can be removed in a diafiltration step, preferably using a nanofiltration membrane as in step ii) disclosed above, to improve the purity of the isolated sialylated oligosaccharide/sialylated lactose salt. Furthermore, the application of anion exchange resin in $HCO_3^-$-form suggested by the prior art is avoidable, which is beneficial in industrial scale operation with regard to feasibility, because the bicarbonate removal by acidification would liberate a significant amount of carbon dioxide gas which may require extra security and technical measures.

In the method of this invention for purifying, preferably isolating, a sialylated oligosaccharide/sialylated lactose, ultrafiltration according to step i) is preferably conducted before any of the steps ii), iii) and iv), and any of the steps ii), iii) and iv) can be applied in any order. In a particularly preferred embodiment, step ii) follows step i).

After the isolation/purification step i), step ii), optional step iii) and step iv), the sialylated oligosaccharide/sialylated lactose so-obtained can be provided in its acidic or salt form. If a solid form of the sialylated oligosaccharide/sialylated lactose is required, it can be spray-dried, freeze-dried or crystallized. Accordingly, the method of the invention may comprise one or more further steps, such as spay-drying an aqueous solution of the sialylated oligosaccharide/sialylated lactose obtained after step i), step ii), optional step iii) or step iv); or freeze-drying an aqueous solution of the sialylated oligosaccharide/sialylated lactose obtained after step i), step ii), optional step iii) or step iv); or crystallising a sialylated oligosaccharide/sialylated lactose from an aqueous solution obtained after step i), step ii), optional step iii) or step iv). Alternatively, the sialylated oligosaccharide/sialylated lactose isolated and purified by the above method may be provided in a form of a concentrated aqueous solution or syrup by removing water, e.g. by means of distillation, preferably vacuum distillation, or nanofiltration.

In a preferred embodiment of the production of a sialylated oligosaccharide/sialylated lactoses by a genetically modified microorganism, the microorganism able to produce a sialylated oligosaccharide is an *E. coli*, preferably of $LacY^+LacZ^-$ genotype carrying neuBCA. The heterologous sialyl transferase gene in the microorganism is preferably an α-2,3- or an α-2,6-sialyl transferase with the aid of which, from the exogenously added lactose as carbohydrate acceptor, 3'-SL or 6'-SL is produced, respectively. Such a microorganism is disclosed e.g. in WO 2007/101862, Fierfort et al. *J. Biotechnol.* 134, 261 (2008) and Drouillard et al. *Carbohydr. Res.* 345, 1394 (2010).

Accordingly, one embodiment of the present invention is a method for isolating a sialylated lactose from a fermentation broth obtained by culturing a genetically modified microorganism capable of producing said sialylated lactose from an internalized lactose, comprising the steps of:

i) ultrafiltration of the broth to obtain an ultrafiltration permeate, ii) nanofiltration of the ultrafiltration permeate to obtain a nanofiltration retentate, iii) activated charcoal treatment of the nanofiltration retentate to obtain a decolorized aqueous solution, and iv) treatment of the aqueous solution of step iii) with a strong anion and/or cation exchange resin.

As a non-limiting example, the isolation yield of 3'-SL from its fermentation broth, produced in accordance with WO 2007/101862 or Fierfort et al. *J. Biotechnol.* 134, 261 (2008), has been improved by the following embodiment of the present method:

i) ultrafiltering the broth, preferably through a 15 kDa membrane, to obtain a UF permeate, followed by a water washing of the UF retentate, wherein the DF is 1.8-3.1, and preferably wherein the CF of the ultrafiltration is 1.25-2.25, ii) nanofiltering, preferably with a 150-300 kDa membrane, the combined UF permeate and water washing filtrate to obtain an NF retentate, iii) adding active charcoal to the NF retentate, preferably powdered active charcoal, more preferably in an amount of 12-25% by mass relative to the 3'-SL content of the NF retentate, to obtain a decolorized aqueous solution, and iv) treating the decolorized solution with an ion exchange resin, which consist of the application of a strong acidic ion exchange resin either in $H^+$-form followed by neutralization of the eluate with NaOH-solution, or in $Na^+$-form, to give rise the sodium salt of 3'-SL.

With the above procedure at least 70% of the 3'-SL produced by fermentation that precedes step i) can be isolated in the purified sodium salt form. The above procedure can be applied to 6'-SL containing fermentation broth with the same performance.

EXAMPLES

Example 1

Ultrafiltration

A fermentation broth containing 3'-SL (340-450 l) was ultrafiltered (15 kDa) at 60-65° C. to collect the UFP with a CF of 1.6-1.7. The UF retentate was then washed with purified water (1.5-2.5-fold volumes relative to the broth volume ultrafiltered) and the suspension was filtered through the same membrane to collect a washing filtrate so that the combined volumes of the UFP and washing filtrate was 1050 l. Analysis showed that 87-96% of 3'-SL contained in the broth was recovered in the combined UFP and washing filtrate.

Example 2

Nanofiltration

The combined UFP and washing filtrate from the previous step (14.6 kg) was nanofiltered applying a 150-300 Da membrane at 20-22 bars and 45° C. until the retentate showed a Brix of about 20-25. Analysis showed that 96% of 3'-SL contained in combined UFP and washing filtrate was recovered in the NF retentate.

Example 3

Active Charcoal Treatment

To a NF retentate made by in accordance with example 1 followed by example 2 (volume range: 200-470 l, concentration range with regard to 3'-SL: 170-210 g/l) powdered active charcoal was added (16-20 w/w % vs. 3'-SL in the NF retentate), and the suspension was stirred for 1 hour. The charcoal was filtered by recirculating the solution until it became clear. The charcoal was washed with water twice (10 l/kg charcoal per wash), and the filtrates were combined. Analysis showed that 91-98% of 3'-SL contained in the NF retentate was recovered in the AC filtrate.

Example 4

Active Charcoal and Ion Exchange Treatment

To a NF retentate made by in accordance with example 1 followed by example 2 with the difference that it contained 6'-SL instead of 3'-SL (201 g solution containing 16.8 g of 6'-SL) powdered active charcoal was added (5 g), and the suspension was stirred for 1 hour. The charcoal was then filtered off and washed with distilled water (40 ml). The combined filtrate (231 g) was divided into two equal parts. The first solution was brought to the top of an Amberlite FPC 22 (H$^+$) ion exchange column (50 ml) and eluted followed by washing the column with distilled water (50 ml). To the eluate NaOH-solution was added (5M, 3.1 ml) to reach a pH of 6.7. The solution was freeze-dried to give 9.24 g of white powder. The second solution was brought to the top of an Amberlite FPC 22 (Na$^+$) ion exchange column (50 ml) and eluted followed by washing the column with distilled water (50 ml). The eluate was freeze-dried to give 9.27 g of white powder.

Assay (by IC): 82.9% (free acid), 90.8% (free acid as water free), 85.7% (Na-salt), 94.0% (Na-salt as water free). Assay (by NMR): 88.9% (free acid), 92.0% (Na-salt). Water content (by KF): 8.8%.

The invention claimed is:

1. A method for separating 3'-sialyllactose (3'-SL) or 6'-sialyllactose (6'-SL) from a fermentation broth obtained by culturing a genetically modified microorganism capable of producing the 3'-SL or 6'-SL from an internalized carbohydrate precursor, wherein the separation comprises the ordered steps of:
   i) ultrafiltration using an ultrafiltration membrane with a molecular weight cutoff from about 5 to 500 kDa, wherein the ultrafiltration is applied to the fermentation broth,
   ii) nanofiltration using a nanofiltration membrane with a molecular weight cut-off lower from about 150 to 300 Da, and
   iii) treatment with strong anion and/or cation exchange resin.

2. The method of claim 1, wherein step i) comprises two consecutive ultrafiltrations.

3. The method of claim 1, wherein step i) further comprises a washing step of the ultrafiltration retentate, to obtain a washing filtrate.

4. The method of claim 1, wherein step i) further comprises the dilution of the fermentation broth prior to ultrafiltration.

5. The method of claim 4, wherein the dilution factor of step i) is 1 to 3.5.

6. The method of claim 1, wherein the ultrafiltration step is characterized by a concentration factor of at least 1.25.

7. The method of claim 1, wherein the ultrafiltration membrane has a molecular weight cut-off of about 5 to 30 kDa.

8. The method of claim 1, wherein the molecular weight cut-off of the nanofiltration membrane in step ii) is around 25-50% of the molecular weight of 3'-SL or 6'-SL.

9. The method of claim 1, wherein the nanofiltration retentate is treated with active charcoal, and wherein the amount of active charcoal applied is about 12-25% by mass relative to the 3'-SL or 6'-SL content of the nanofiltration retentate.

10. The method of claim 1, wherein a strong cation exchange resin in H$^+$-form is used in step iii) followed by addition of an alkaline solution to the eluent to obtain an alkaline salt of 3'-SL or 6'-SL.

11. The method of claim 1, wherein a strong cation exchange resin in monovalent alkaline cation form is used in step iii) to obtain an alkaline salt of 3'-SL or 6'-SL.

12. The method of claim 1, wherein 3'-SL is separated from the fermentation broth.

13. The method of claim 1, wherein the genetically modified microorganism is an *E. coli* of LacY$^+$LacZ$^-$ genotype.

14. The method of claim 13, wherein the *E. coli* comprises a recombinant α-2,3- or α-2,6-sialyl transferase.

15. The method of claim 14, wherein the *E. coli* carries neuBCA genes.

16. The method of claim 3, wherein the combined ultrafiltration permeate and washing filtrate is treated with active charcoal, and wherein the amount of active charcoal applied is about 12-25% by mass relative to the sialylated oligosaccharide content of the combined ultrafiltration permeate and washing filtrate.

17. The method of claim 1, wherein the ultrafiltration permeate obtained from step i) is treated with active charcoal, and wherein the amount of active charcoal applied is about 12-25% by mass relative to the sialylated oligosaccharide content of the ultrafiltration permeate.

18. The method of claim 1, wherein the ultrafiltration step i) is preceded by a pH-adjustment step comprising adjusting the pH of the fermentation broth to around 4 to 5.5.

19. The method of claim 1, wherein 6'-SL is separated from the fermentation broth.

20. The method of claim 1, wherein the ultrafiltration step i) is preceded by an activated charcoal step, wherein the activated charcoal step comprises adding activated charcoal to the fermentation broth.

* * * * *